United States Patent

Santora et al.

[11] Patent Number: 6,046,145
[45] Date of Patent: Apr. 4, 2000

[54] CLEANSING AND MOISTURIZING SURFACTANT COMPOSITIONS

[75] Inventors: Delores M. Santora, Somerville, N.J.;
Diana L. Friscia, Fairless Hills, Pa.

[73] Assignee: Johnson & Johnson Consumer Companies, Inc., Skillman, N.J.

[21] Appl. No.: 09/271,760

[22] Filed: Mar. 18, 1999

Related U.S. Application Data

[63] Continuation of application No. 08/816,582, Mar. 13, 1997
[60] Provisional application No. 60/013,390, Mar. 14, 1996.
[51] Int. Cl.$^7$ .................................................... C11D 1/94
[52] U.S. Cl. ................... 510/121; 510/124; 510/126; 510/127; 510/470
[58] Field of Search ............................ 510/121, 124, 510/126, 127, 470

[56] References Cited

U.S. PATENT DOCUMENTS

| | | | |
|---|---|---|---|
| 3,962,418 | 6/1976 | Birkofer | 424/70 |
| 4,110,263 | 8/1978 | Lindemann et al. . | |
| 4,181,634 | 1/1980 | Kennedy et al. . | |

(List continued on next page.)

FOREIGN PATENT DOCUMENTS

| | | |
|---|---|---|
| 88005/82 | 3/1983 | Australia . |
| 23880/84 | 8/1984 | Australia . |
| 86967/91 | 5/1992 | Australia . |
| 15224/92 | 11/1992 | Australia . |
| 68887/94 | 9/1995 | Australia . |
| 2006248 | 6/1990 | Canada . |
| 2054898A1 | 5/1992 | Canada . |
| 2122272A1 | 5/1993 | Canada . |
| 2095743A1 | 11/1993 | Canada . |
| 2161008A1 | 10/1994 | Canada . |
| 0 166 089 | 2/1986 | European Pat. Off. . |
| 194593 | 11/1984 | New Zealand . |
| 213496 | 4/1988 | New Zealand . |
| 223531 | 3/1989 | New Zealand . |

(List continued on next page.)

OTHER PUBLICATIONS

International Search Report, PCT WO 9733561, Sep. 1997.

*Primary Examiner*—Mark Kopec
*Assistant Examiner*—John R. Hardee
*Attorney, Agent, or Firm*—Michele G. Mangini

[57] ABSTRACT

Cleansing surfactant compositions are provided which cleanse, condition and moisturize the skin and hair and which exhibit a low degree of irritation to the eyes. These cleansing compositions preferably contain the following components:

a. a surfactant portion containing:
  1. a nonionic surfactant;
  2. an amphoteric surfactant; and
  3. an anionic surfactant;

the total concentration of said nonionic, amphoteric and anionic surfactants being present in the composition in an amount from about 5 to about 20 percent by weight of said cleansing composition; and b. a substantive humectant present in the composition in an amount from about 0.01 to about 3 percent by weight of said cleansing composition.

The substantive humectants used in the present invention are preferably cationically charged polyols derived from sugars or sugar derivatives and they further comprise a long chain alkyl or alkenyl group having from about 6 to about 22 carbon atoms.

14 Claims, 1 Drawing Sheet

U.S. PATENT DOCUMENTS

| | | |
|---|---|---|
| 4,375,421 | 3/1983 | Rubin et al. . |
| 4,420,410 | 12/1983 | Huttinger . |
| 4,426,310 | 1/1984 | Verunica . |
| 4,435,300 | 3/1984 | Guth et al. . |
| 4,497,825 | 2/1985 | Bade . |
| 4,529,588 | 7/1985 | Smith et al. ............................... 424/70 |
| 4,654,207 | 3/1987 | Snyder . |
| 4,708,813 | 11/1987 | Snyder . |
| 4,717,501 | 1/1988 | Hirota et al. . |
| 4,726,915 | 2/1988 | Verdicchio . |
| 4,772,424 | 9/1988 | Greeb . |
| 4,806,262 | 2/1989 | Snyder . |
| 4,824,594 | 4/1989 | Hoeffkes et al. . |
| 4,861,517 | 8/1989 | Bade . |
| 4,931,216 | 6/1990 | Igarashi et al. . |
| 4,938,953 | 7/1990 | Pena et al. . |
| 4,948,528 | 8/1990 | Hoeffkes et al. . |
| 4,997,641 | 3/1991 | Hartnett et al. . |
| 5,002,680 | 3/1991 | Schmidt et al. . |
| 5,057,246 | 10/1991 | Bertho et al. . |
| 5,106,613 | 4/1992 | Hartnett et al. . |
| 5,130,056 | 7/1992 | Jakobson et al. ........................ 252/551 |
| 5,284,603 | 2/1994 | Repinec, Jr. et al. ................... 252/546 |
| 5,290,482 | 3/1994 | Marschner et al. ...................... 252/544 |
| 5,385,696 | 1/1995 | Repinec, Jr. et al. ................... 252/546 |
| 5,387,375 | 2/1995 | Erilli et al. ............................... 252/546 |
| 5,389,304 | 2/1995 | Repinec, Jr. et al. ................... 252/546 |
| 5,389,305 | 2/1995 | Repinec, Jr. et al. ................... 252/346 |
| 5,403,508 | 4/1995 | Reng et al. ............................... 252/174 |
| 5,474,776 | 12/1995 | Koyanagi et al. ........................ 424/401 |
| 5,490,955 | 2/1996 | Hagan et al. ............................. 252/554 |
| 5,496,492 | 3/1996 | Hamada et al. .......................... 252/170 |
| 5,576,027 | 11/1996 | Friedman et al. ........................ 424/535 |
| 5,612,024 | 3/1997 | Giede et al. ........................... 424/70.11 |

FOREIGN PATENT DOCUMENTS

| | | |
|---|---|---|
| 227813 | 3/1990 | New Zealand . |
| 218118 | 6/1990 | New Zealand . |
| 225690 | 10/1990 | New Zealand . |
| 234188 | 9/1993 | New Zealand . |
| 234794 | 1/1994 | New Zealand . |
| 234795 | 1/1994 | New Zealand . |
| 234797 | 1/1994 | New Zealand . |
| 239982 | 2/1994 | New Zealand . |
| 239050 | 6/1994 | New Zealand . |
| 247675 | 10/1994 | New Zealand . |
| 241862 | 2/1995 | New Zealand . |
| 247677 | 4/1995 | New Zealand . |
| 244862 | 7/1995 | New Zealand . |
| 2 297 761 | 8/1996 | United Kingdom . |
| WO93/18737 | 9/1993 | WIPO . |
| WO95/00616 | 6/1994 | WIPO . |
| WO94/21767 | 9/1994 | WIPO . |
| WO94/21768 | 9/1994 | WIPO . |
| WO95/00620 | 1/1995 | WIPO . |
| WO95/02664 | 1/1995 | WIPO . |
| WO95/23204 | 8/1995 | WIPO . |
| WO96/02224 | 2/1996 | WIPO . |
| WO96/02225 | 2/1996 | WIPO . |
| WO96/02230 | 2/1996 | WIPO . |

FIG. 1

CLEANSING AND MOISTURIZING SURFACTANT COMPOSITIONS

CROSS-REFERENCE TO RELATED APPLICATION

This application is a continuation application of U.S. application Ser. No. 08/816,582, filed Mar. 13, 1997, which claims the benefit of U.S. Provisional Application Ser. No. 60/013,390 filed on Mar. 14, 1996, which are both incorporated by reference in their entireties.

FIELD OF THE INVENTION

This invention relates to cleansing surfactant compositions which cleanse, condition and moisturize the skin and hair and which exhibit a low degree of irritation to the eyes. The compositions are especially useful for cleansing the skin and hair of infants and young children and adults with sensitive skin and eyes.

BACKGROUND OF THE INVENTION

Cleansing surfactant compositions are designed to remove accumulated soil and oils from the skin and hair. Unfortunately, these compositions often exhibit a number of drawbacks. The first of these is that upon total removal of skin and hair oils, the skin and hair are made to feel excessively and uncomfortably dry. The second drawback with many cleansing compositions is that the surfactants or other components of the composition contain ingredients that are irritating to the eyes, which is especially troublesome when the products are used on infants, children and adults with sensitive eyes and skin.

One method used by the cosmetics and toiletries industry to overcome the problem of dryness is to add moisturizers to the cleansing product. Unfortunately, this method often provides a product which leaves the body with an excessively oily and slippery residue when the composition is washed from the body. Furthermore, even starting with a surfactant base that has a low degree of eye irritation, the presence of added components such as moisturizers can upset the ocular mildness of the overall formulation. The presence of moisturizers in surfactant compositions also has a tendency to reduce the dispersibility and foamability of the composition, which negatively impacts the consumer acceptance of the product. Accordingly, it is an object of this invention to provide a cleansing composition that is exceedingly mild to the skin and to the eyes. It is another object of this invention to provide a cleansing composition that does not leave the skin with an excessively dry feeling. It is another object of this invention to provide a cleansing composition that leaves the skin and hair feeling moist but without feeling excessively oily and slippery. It is another object of this invention to provide a moisturizing cleansing composition which does not leave a slippery and oily residue on bath surfaces. It is another object of the invention to provide a moisturizing cleansing composition that is not adversely affected as to the attributes of dispersibility and foamability.

Finally, it is an object of this invention to provide a cleansing composition with the combination of attributes of mildness to the skin and eyes and effective cleansing, while leaving the skin with a feel that is neither excessively dry nor oily.

SUMMARY OF THE INVENTION

The present invention relates to cleansing surfactant compositions which cleanse, condition and moisturize the skin and hair and which exhibit a low degree of irritation to the eyes. Skin and hair cleansing surfactant compositions of this invention clean the skin and hair without imparting a feeling of excessive dryness or oiliness. The compositions are especially useful for cleansing the skin and hair of infants and young children and adults with sensitive skin and eyes. The compositions of the present invention achieve their properties as a result of specific combinations of surfactants and substantive humectants which result in excellent cleansing without imparting a feeling of excessive dryness or oiliness to the skin and hair. The compositions of the present invention achieve these cleansing and moisturizing benefits while being relatively non-irritating to the eyes. The cleansing compositions of the present invention preferably contain the following components:

a. a surfactant portion containing:
   1. a nonionic surfactant;
   2. an amphoteric surfactant; and
   3. an anionic surfactant;

the total concentration of said nonionic, amphoteric and anionic surfactants being present in the composition in an amount from about 5 to about 20 percent by weight of said cleansing composition; and b. a substantive humectant present in the composition in an amount from abut 0.01 to about 3 percent by weight of said cleansing composition.

The substantive humectant used in the present invention is cationically charged, thereby being capable of binding to the negatively charged sites on the skin and the hair. The negatively charged sites on skin and hair attract the positively charged humectant molecules, promoting a moist feeling on skin and hair cleaned with the composition of the present invention. The moisturized feeling is retained even after the cleansing composition is rinsed off, and this feeling is maintained for extended periods of time. Furthermore, this cleansed and moisturized feeling is achieved without the oily feel provided by conventional moisturizing agents. Despite the fact that additives to surfactant compositions often upset the ocular mildness of such formulations, the cleansing compositions of the present invention surprisingly retain their ocular mildness in the presence of the substantive humectants used in the compositions of the present invention. The substantive humectants used in the present invention are preferably cationically charged polyols. Preferred humectants are derived from sugars or sugar derivatives. More preferably, the cationic polyol is an alkoxylated derivative of methyl glucoside. Most preferably, the humectants used in the compositions of the present invention further comprise a long chain alkyl or alkenyl group having from 6 to 22 carbon atoms.

DETAILED DESCRIPTION OF THE INVENTION

DESCRIPTION OF THE PREFERRED EMBODIMENTS

The cleansing compositions of the present invention comprise, consist essentially of, and/or consist of the following components:

a. a surfactant portion containing:
1. a nonionic surfactant;
2. an amphoteric surfactant; and
3. an anionic surfactant;

the total concentration of said nonionic, amphoteric and anionic surfactants being present in the composition in an amount from about 5 to about 20 percent by weight of said cleansing composition; and b. a substantive humectant present in the composition in an amount from about 0.01 to about 3, and preferably from about 0.1 to about 0.5 percent by weight of said cleansing composition.

The nonionic surfactant material is preferably selected from the following materials and may be composed of one or more of the following: (a) polyoxyethylene derivatives of polyol esters, wherein (1) the polyoxyethylene derivative of polyol ester is derived from a polyol selected from the following group: sorbitol, sorbitan, glucose, α-methyl glucoside, polyglucose having an average of about 1.1 to about 3 glucose residues, glycerine, pentaerythritol and mixtures thereof; (2) the polyoxyethylene derivative of polyol ester contains from about 10 to about 120 oxyethylene units; (3) the polyoxyethylene derivative of polyol ester is derived from a fatty acid containing from about 8 to about 22 carbon atoms; and (4) the polyoxyethylene derivative of polyol ester has from 1 to 2 fatty acid residues per mole of polyoxyethylene derivative of polyol ester; (b) an alkyl polyglucoside; and mixtures thereof.

The nonionic surfactant should be present in the cleansing composition in an amount of about 1 to about 10 weight percent of the composition.

The compositions of the present invention also contain an amphoteric surfactant. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines, amidoalkyl betaines, and mixtures thereof. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

The amphoteric surfactant materials useful in the compositions of this invention may include one or more of the following surfactants: (a) an amphocarboxylate compound of the formula R—CONH (CH$_2$)$_x$N$^+$R$_1$R$_2$R$_3$ wherein R is an alkyl group having 7 to 17 carbon atoms, x is an integer from 1 to 6, R$_1$ is hydrogen or a carboxyalkyl group containing from 2 to 3 carbon atoms, R$_2$ is a hydroxyalkyl group containing from 2 to 3 carbon atoms or a group of the formula:

R$_4$—O—(CH$_2$)$_n$CO$_2^-$ wherein R$_1$ is a 2 to 3 carbon alkylene group and n is either 1 or 2, and R$_3$ is a carboxyalkyl group containing from 2 to 3 carbon atoms; (b) an alkyl betaine of the formula:

R—N$^+$R$_1$R$_2$(CH$_2$)$_n$CO$_2^-$ wherein R is an alkyl group having from 8 to 18 carbon atoms, R$_1$ and R$_2$ are each alkyl groups having from 1 to 4 carbon atoms and n is either 1 or 2; (c) an amidoalkyl betaine of the formula:

R—CO—NH(CH$_2$)$_n$—N$^+$R$_1$R$_2$(CH$_2$)$_m$CO$_2^-$ wherein R is an alkyl group having from 7 to 17 carbon atoms, R$_1$ and R$_2$ are each alkyl groups having from 1 to 4 carbon atoms, n is an integer from 2 to 6 and m is either 1 or 2; and mixtures thereof. The amphoteric surfactant should be present in the shampoo composition at a concentration from about 0.5 to about 10 percent by weight.

Preferably, the anionic surfactant for use in the compositions of the present invention can be one or more of the following surfactants:

(a) an alkyl sulfate of the formula:

R—CH$_2$OSO$_3$X, (b) an alkyl ether sulfate of the formula:

R(OCH CH)$_n$OSO$_3$X, (c) an alkyl monoglyceryl ether sulfate of the formula:

ROCH$_2$—CH—CH$_2$—OSO$_3$X
        |
        OH (d) an alkyl monoglyceride sulfate of the formula:

RCO$_2$—CH—CH$_2$—OSO$_3$X
       |
       OH (e) an alkyl monoglyceride sulfonate of the formula:

RCO$_2$—CH—CH$_2$—SO$_3$X
       |
       OH

(f) an alkyl sulfonate of the formula:

R—SO X, (g) an alkylaryl sulfonate of the formula:

(h) an alkylaryl sulfonate of the formula:

R(OCH$_2$CH$_2$)$_p$O(CH$_2$)$_n$CO$_2$X, and mixtures thereof, wherein R is an alkyl group having 7 to 17 carbon atoms, $R_1$ is H or an alkyl group having 1 to 17 carbon atoms, X is selected from alkali metal ions, alkaline earth metal ions, ammonium ions, and ammonium ions substituted with from 1 to 3 substituents, each of which may be the same or different, and each of said substituents being selected from alkyl groups having from 1 to 4 carbon atoms and hydroxyalkyl groups having from 2 to 4 carbon atoms, and p is an integer from 1 to 6.

The anionic surfactant is preferably present in the cleansing composition at a concentration from about 1 to about 10 percent by weight.

The substantive humectant used in the compositions of this invention is preferably a cationic polyol. The cationic charge on the humectant makes the humectant substantive to the negative charges on skin and hair. Preferably, the polyol is derived from a sugar or sugar derivative. Examples of polyols useful for making the substantive humectants used in this invention are alkoxylated alkyl glucosides. Most preferably, the substantive humectant further contains a long chain alkyl group having from about 6 to about 22 carbon atoms.

A preferred substantive humectant which is a positively charged polyol derived from alkyl glucoside and which contains a long chain alkyl group is of the formula wherein w+x+y+z=5 to 20, R is an alkyl or alkenyl group having 6 to 22 carbon atoms, $R_1$, $R_2$ and $R_3$ are each independently lower alkyl having from 1 to 4 carbon atoms and wherein X is halide, carboxylate or alkyl sulfate.

More preferred compositions of the present invention contain the following components:
 a. a surfactant portion containing:
  1. nonionic surfactant;
  2. amphocarboxylate amphoteric surfactant;
  3. betaine amphoteric surfactant; and
  4. anionic surfactant;
 the total concentration of said nonionic, amphocarboxylate, betaine and anionic surfactants being present in the composition in an amount from about 5 to about 20 percent by weight of said cleansing composition; and
 b. a substantive humectant present in the composition in an amount from about 0.01 to about 3 percent by weight of said cleansing composition.

The nonionic surfactant material in the more preferable compositions of the invention are more preferably selected from the following materials and may be composed of one or more of the following: (a) polyoxyethylene derivatives of polyol esters, wherein (1) the polyoxyethylene derivative of polyol ester is derived from a polyol selected from the following group: sorbitol, sorbitan, glucose, α-methyl glucoside, polyglucose having an average of about 1.1 to about 3 glucose residues, glycerine, pentaerythritol and mixtures thereof; (2) the polyoxyethylene derivative of polyol ester contains from about 10 to about 120 oxyethylene units; (3) the polyoxyethylene derivative of polyol ester is derived from a fatty acid containing from about 8 to about 22 carbon atoms; and (4) the polyoxyethylene derivative of polyol ester has from 1 to 2 fatty acid residues per mole of polyoxyethylene derivative of polyol ester. The more preferred compositions of the invention contain from about 1 to about 10 percent by weight of the more preferred nonionic surfactants.

The surfactant portion of the more preferred compositions of this invention should contain a mixture of amphocarboxylate and alkyl betaine or amidoalkyl betaine, wherein the amphocarboxylate, alkyl betaine and amidoalkyl betaine are as hereinbefore defined. The amphocarboxylate is present in the composition at a concentration from about 0.25 to about 10 percent by weight and the alkyl betaine or amidoalkyl betaine being present in the composition at a concentration of from about 0.25 to about 10 percent by weight.

The anionic surfactant used in the more preferable compositions of this invention contains one or more of the following surfactants:

alkyl ether sulfate of the formula wherein R is an alkyl group having 7 to 17 carbon atoms, X is selected from alkali metal ions, alkaline earth metal ions, ammonium ions, and ammonium ions substituted with from 1 to 3 substituents, each of said substituents being the same or different, and each of which are selected from alkyl groups having from 1 to 4 carbon atoms and hydroxyalkyl groups having from 2 to 4 carbon atoms, and p is an integer from 1 to 6. The more preferred anionic surfactants are present in the more preferred compositions of the invention at a concentration of 1.0 to 10 percent by weight.

The more preferred compositions of this invention contain a substantive humectant which is a positively charged polyol derived from alkyl glucoside and which contains a long chain alkyl group and which is of the formula wherein w+x+y+z=5 to 20, R is an alkyl or alkenyl group having 6 to 22 carbon atoms, $R_1$, $R_2$ and $R_3$ are each independently lower alkyl having from 1 to 4 carbon atoms and wherein X is halide, carboxylate or alkyl sulfate. The substantive humectant is present in the compositions of the invention at a concentration of about 0.01 to about 3.0 percent by weight.

The most preferred compositions of the present invention contain the following components:
 a. a surfactant portion containing:
  1. nonionic surfactant;
  2. amphocarboxylate amphoteric surfactant;
  3. betaine amphoteric surfactant; and
  4. anionic surfactant;
 the total concentration of said nonionic, amphocarboxylate, betaine and anionic surfactants being present in the composition in an amount from about 5 to about 20 percent by weight of said cleansing composition;
b. a substantive humectant present in the composition in an amount from about 0.01 to about 3 percent by weight of said cleansing composition; and
c. a thickener is an amount from about 0.1 to about 3.0 percent by weight of the composition.

The nonionic surfactant in the most preferred compositions of the invention most preferably consist of a polyoxyethylene derivative of polyol ester wherein (1) the polyoxyethylene derivative of polyol ester is derived from a polyol selected from sorbitol, sorbitan and mixtures thereof, (2) the polyoxyethylene derivative of polyol ester contains from 20 to 80 oxyethylene units, (3) the polyoxyethylene derivative of polyol ester is derived from lauric acid, and (4) the polyoxyethylene derivative of polyol ester has from 1 to 2 lauric acid residues per molecule of polyoxyethylene derivative of polyol ester.

The most preferred compositions of the invention contain from about 2 to about 10 percent by weight of these most preferred nonionic surfactants.

Examples of nonionic surfactants which are most preferred for use in the compositions of this invention are as follows:

PEG-80 sorbitan laurate is an ethoxylated derivative of sorbitan monoester of lauric acid ethoxylated with an average of 80 moles of ethylene oxide. The material known as Atlas G4280, available from ICI Chemicals Americas of Wilmington, Del., is one preferred nonionic surfactant for use in the compositions of the invention.

Yet another surfactant which can be used in the compositions of this invention is Polysorbate 20, the mixture of laurate esters of sorbitol and sorbitol anhydrides, consisting predominantly of the monoester, condensed with approximately 20 moles of ethylene oxide. The material known as Tween 20, available from ICI Chemicals Americas, Wilmington, Del., is another preferred material for use in the present compositions.

The most preferable compositions of the invention contain a mixture of both amphocarboxylate and betaine surfactants. The amphocarboxylate surfactant is most preferably a compound of the formula wherein R is an alkyl group having 11 carbon atoms, x is 2, $R_1$ is hydrogen, $R_2$ is a group of the formula wherein $R_4$ is a 2 carbon alkylene group and $R_1$ is a carboxymethyl group, and wherein the amphocarboxylate surfactant is present in the cleansing composition at a concentration from about 0.25 to about 5 percent by weight. An illustrative example of the most preferred amphocarboxylate compound for use in the present invention is Monateric 849-J otherwise known as disodium lauroamphodiacetate having the formula available from Mona Chemical Company of Paterson, N.J. Another amphocarboxylate useful in the compositions of the present invention is Miranol BM available from Rhone-Poulenc of Cranbury, N.J.

Most preferably, the betaine surfactant used in the present invention is selected from (1) an alkyl betaine of the formula wherein R is a lauryl group having 12 carbon atoms, and $R_1$ and $R_2$ are each methyl groups, i.e., of the formula and (2) an amidoalkyl betaine of the formula wherein RCO represents the fatty acid derived from coconut oil, n is 3 and $R_1$ and $R_2$ are each methyl groups, i.e., of the formula wherein RCO represents the fatty acid derived from coconut oil. The betaine surfactant is most preferably present in the cleansing composition at a concentration from about 0.5 to about 8 percent by weight.

Illustrative examples of the most preferred betaines used in the present invention are Tegobetaine L-7 which is known by its International Nomenclature Cosmetic Ingredient (INCI) name as cocamidopropyl betaine and is available from Goldschmidt Chemical Company of Hopewell, Va. Another illustrative preferred betaine for use in this invention is lauryl betaine which is available as Empigen BB from Albright & Wilson Americas of Richmond, Va.

The most preferred compositions of the present invention contain one or more alkyl ether sulfate anionic surfactants of the formula wherein R is an alkyl group having 12 to 13 carbon atoms, X is sodium ion and p is an integer from 1 to 4.

The anionic surfactant is most preferably present in the compositions of the present invention at a concentration from about 1 to about 8 percent by weight.

An example of these most preferred anionic surfactants is sodium laureth sulfate of the formula wherein n averages between 1 and 4, sold under the name of Empicol 0251/70 by Albright & Wilson Americas of Richmond, Va. Another preferred anionic surfactant is sodium trideceth sulfate of the formula wherein n averages between 1 and 4, solid under the name Cedepal TD-403 by Stepan Chemical Company of Chicago, Ill.

In addition to the alkyl ether sulfates, preferred compositions of this invention also contain alkyl ether carboxylates of the formula:

$$R(OCH_2CH_2)_pO(CH_2)_nCO_2X$$

wherein R, p, n and X are as defined above. A most preferred alkyl ether carboxylate for use in this invention is sodium laureth-13 carboxylate sold under the name Sandopan LS-24 by Sandoz Chemicals Corporation of Charlotte, N.C.

The most preferred compositions of this invention contain a substantive humectant which is a positively charged polyol derived from alkyl glucoside and which contains a long chain alkyl group and which is of the formula:

wherein w+x+y+z=10. This material is available as Glucquat 125 from the Amerchol corporation of Edison, N.J. The substantive humectant is present in the most preferred compositions of the invention at a concentration of about 0.1 to about 0.5 percent by weight.

A thickening agent is also useful in the compositions of this invention in order to impart the appropriate viscosity to the compositions of the invention. A thickener may be selected from the following:

(a) mono or diesters of fatty acids containing from 16 to 22 carbon atoms with polyethylene glycol of the formula:

$$HO-(CH_2CH_2)_nH$$

wherein n is an integer from 3 to 200:

(b) fatty acid esters of ethoxylated polyols;

(c) ethoxylated derivatives of mono and diesters of fatty acids and glycerine;

(d) hydroxyalkyl cellulose;

(e) alkyl cellulose; and (f) hydroxyalkyl alkyl cellulose.

The thickener may be present in the compositions of the invention at a concentration of about 0.1 to about 5 percent by weight, more preferably at a concentration of about 0.1 to about 3.0 percent by weight. Polyethylene glycol esters are preferable thickeners for use in the compositions of the invention. PEG-150 distearate is the thickener for use in the most preferred compositions of this invention. This material is available as Kessco PEG 6000 Distearate from the Stepan company of Northfield, Ill.

Inorganic slats may also be used as thickeners instead of or in addition to the organic thickeners mentioned above. Sodium chloride is a preferred inorganic salt in this regard. It may be added to the compositions of the invention at a concentration of about 0.5 to about 5 percent by weight, and preferably, at a concentration of about 1 to about 3 percent by weight.

The cleansing compositions of this invention may also optionally contain one or more nonsubstantive humectants selected from:

(a) water soluble liquid polyols selected from the group consisting of glycerine, propylene glycol, hexylene glycol, butylene glycol and dipropylene glycol;

(b) polyethylene glycol of the formula $$HO-(RO)_n-H$$

wherein R is a 2 or 3 carbon alkylene group and n is 2 to 10;

(c) polyethylene glycol ether of methyl glucoside of formula wherein w+x+y+z=5 to 25, (d) urea, and mixtures thereof.

The nonsubstantive humectant may be present in the cleansing composition at a concentration of about 0.1 to about 5 percent by weight.

A most preferred nonsubstantive humectant is glycerin, which is preferably present in the composition at a concentration of 0.25 to 1.5 percent by weight.

Also useful in the compositions of this invention is a pearlizer, which tends to communicate positive attributes about the product to the consumer. The pearlescent or opacifying agent can be selected from the following group:

(a) mono- or diesters of fatty acids having 16 to 22 carbon atoms with ethylene or propylene glycol, (b) mono- or diesters of fatty acids having 16 to 22 carbon atoms with a polyalkylene glycol of the formula:

$$HO-(RO)_n-H$$

wherein R is a 2 or 3 carbon alkylene group and n is 2 or 3;

(c) fatty alcohols containing 16 to 22 carbon atoms;

(d) fatty esters of the formula:

$$RCOOCH_2R_1$$

wherein R and $R_1$ each contain from 15 to 21 carbon atoms;

(e) inorganic solids insoluble in the cleansing composition; and mixtures thereof.

The pearlescent or opacifying agent may be present in the composition at a concentration of from about 0.25 to about 2.5 percent by weight. The inorganic pearlizing or opacifying agents can be titanium dioxide or mica.

A preferred pearlizer is a diester of fatty acids having 16 to 22 carbon atoms with ethylene or propylene glycol. Most preferred as a pearlizer is ethylene glycol distearate.

The pearlizer is most conveniently added to the composition of the invention as a preformed, stabilized aqueous dispersion. An example of a preferred preformed pearlizer is Euperlan PK-3000, available commercially from Henkel Corporation of Hoboken, N.J., which is a combination of glycol distearate, Laureth-4 and cocamidopropyl betaine. Generally, Euperlan PK-3000 contains about 25–30% of glycol distearate, 3–15% of Laureth-4 and between about 20–25% of cocamidopropyl betaine.

The compositions of the present invention may also contain one or more additives such as plant extracts, plant homogenates, plant juices, vitamins and vitamin derivatives. For example, aloe vera gel, the mucilage obtained as the juice expressed from the leaves of the *Aloe barbadensis* Miller plant, is generally believed to soothe irritated skin, and may be advantageously added to the compositions of this invention. One source of aloe vera gel is Aloe-Con UP-40, a 40-fold aloe vera gel concentrate available from Florida Food Products of Eustis, Fla. Due to its concentrated state, the addition of one part of this concentrate to formulation is equivalent to adding 40 parts of aloe vera gel to the formulation. Similarly, anti-oxidant and anti-inflammatory properties are attributed to vitamin E and its derivatives, which may be also beneficially added to compositions of this invention.

The compositions of this invention may also contain additives which enhance their appearance, feel and fragrance, such as colorants, fragrances, preservatives and pH adjusting agents. Chelating agents such as EDTA are also helpful in protecting and preserving the compositions of this invention. A chelating agent such as tetrasodium EDTA, available commercially as Versene 100XL, from Dow Chemical company of Midland, Mich., may be used. Preservatives such as quaternium-15, available commercially as Dowicil 200 from the Dow Corporation of Midland, Mich., may be used.

The pH of the compositions of this invention should be in the range of from about 5 to about 7.5.

Compositions which illustrate the preferred compositions of this invention are shown in the following examples.

TABLE 1

Example 1

| Ingredient Trade Name* | Component INCI Name | % Active | % (w/w) | % Active (w/w) |
|---|---|---|---|---|
| Water | Water | 100 | 62.1 | 62.1052 |
| Tegobetaine L-7 | Cocamidopropyl Betaine | 30 | 12.5 | 3.75 |
| Cedepal TD 403 | Sodium Trideceth Sulfate | 30 | 9.00 | 2.7 |
| Monateric 949-J | Disodium Lauroamphodiacetate | 30 | 2.70 | |
| Glucquat 125 | Lauryl Methyl Gluceth-10 | 25 | 1.00 | 0.25 |
| Atlas G-4280 | Hydroxypropyl Dimonium Chloride PEG (80) Sorbitan Monolaurate | 72 | 6.30 | 4.536 |
| Sandopan LS-24 | Sodium Laureth-13 Carboxylate | 70 | 0.45 | 0.315 |
| Culinox 999 | Sodium Chloride | 100 | 2.00 | 2 |
| PEG 6000 Distearate | PEG-150 Distearate | 100 | 0.400 | 0.4 |
| Euperlan PK 3000* | | | 2.50 | |
| | Glycol Distearate (and) | * | | 0.625 |
| | Laureth-4 (and) | * | | 0.3 |
| | Cocamidopropyl Betaine | * | | 0.56 |
| Dowicil 200 | Quaternium-15 | 100 | 0.050 | 0.05 |
| Versene 100 XL | Tetrasodium EDTA | 38 | 0.250 | 0.095 |
| Aloe Con UP-40 Cos** | Aloe Vera Gel | **Concentrate | 0.010 | 0.4 |
| Vitamin E Acetate | Tocopheryl Acetate | 100 | 0.010 | 0.01 |
| Fragrance | Fragrance | 100 | 0.200 | 0.2 |
| Glycerin | Glycerin, 99% | 99 | 0.500 | 0.495 |
| Citric Acid, USP | Citric Acid, USP | 100 | 0.025 | 0.0248 |

*Euperlan PK 3000 is a mixture containing approixmately 25–30% ethylene glycol distearate, 8–15% laureth-4 and 20–25% cocamidopropyl betaine.
**Aloe Con UP-40 Cos is a 40-fold concentrate. 0.01% Aloe CON added to the formulation is equivalent to 0.4% Aloe Vera Gel in the formulation.

TABLE 2

Example 2

| Ingredient Trade Name* | Component INCI Name | % Active | % (w/w) | % Active (w/w) |
|---|---|---|---|---|
| Water | Water | 100 | 70.5 | 70.5 |
| Empigen BB | Lauryl Betaine | 30 | 2.0 | 0.6 |
| Empicol 0251/70 | Sodium Laureth Sulfate | 70 | 4.26 | 2.98 |
| Monateric 949-J | Disodium Lauroamphodiacetate | 27 | 8.28 | 2.24 |
| Glucquat 125 | Lauryl Methyl Gluceth-10 Hydroxypropyl Dimonium Chloride | 25 | 1.00 | 0.25 |
| Polysorbate 20 | PEG (20) Sorbitan Monolaurate | 72 | 5.30 | 3.82 |
| Culinox 999 | Sodium Chloride | 100 | 2.00 | 2.0 |
| PEG 6000 Distearate | PEG-150 Distearate | 100 | 2.00 | 2.0 |
| Genopol 437-X* |  |  | 2.50 |  |
|  | Glycol Distearate (and) | * |  | 0.5 |
|  | Cocamide MEA/DEA (and) | * |  | 0.13 |
|  | Cocamidopropyl Betaine | * |  | 0.15 |
| Dowicil 200 | Quaternium-15 | 100 | 0.050 | 0.05 |
| Versene 100 XL | Tetrasodium EDTA | 38 | 0.250 | 0.095 |
| Aloe Con UP-40 Cos** | Aloe Vera Gel | **Concentrate | 0.010 | 0.4 |
| Vitamin E Acetate | Tocopheryl Acetate | 100 | 0.010 | 0.01 |
| Fragrance | Fragrance | 100 | 0.300 | 0.3 |
| Glycerin | Glycerin, 99% | 99 | 0.500 | 0.485 |
| Citric Acid, USP | Citric Acid, USP | 100 | 0.028 | 0.028 |

*Genapol 437-X is a mixture containing approximately 20% ethylene glycol distearate, 6% cocamidopropyl betaine and about 5% cocamide monoethanolamide/diethanolamide.
**Aloe Con UP-40 Cos is a 40-fold concentrate. 0.01% Aloe CON added to the formulation is equivalent to 0.4% Aloe Vera Gel in the formulation.

TABLE 3

| Example Ingredient Trade Name* | 3 | 4 | 5 | 6 % (w/w) | 7 | 8 | 9 |
|---|---|---|---|---|---|---|---|
| Tegobetaine L-7 | 12.5 | 5.3 | 21.2 | 12.5 | 12.5 | 12.5 | 12.5 |
| Cedepal TD 403 | 9.00 | 3.8 | 19.2 | 9.00 | 9.00 | 9.00 | 9.00 |
| Monateric 949-J | 2.70 | 1.1 | 4.4 | 2.70 | 2.70 | 2.70 | 2.70 |
| Glucquat 125 | 1.00 | 1.00 | 1.00 | 0.04 | 12.0 | 0.4 | 2.0 |
| Atlas G-4280 | 6.30 | 2.7 | 10.8 | 6.30 | 6.30 | 6.30 | 6.30 |
| Sandopan LS-24 | 0.45 | 0.45 | 0.45 | 0.45 | 0.45 | 0.45 | 0.45 |
| Culinox 999 | 2.00 | 2.00 | 2.00 | 2.00 | 2.00 | 2.00 | 2.00 |
| PEG 6000 Distearate | 0.400 | 0.400 | 0.400 | 0.400 | 0.400 | 0.400 | 0.400 |
| Euperlan PK 3000* | — | 2.5 | 2.5 | 2.5 | 2.5 | 2.5 | 2.5 |
| Dowicil 200 | 0.050 | 0.050 | 0.050 | 0.050 | 0.050 | 0.050 | 0.050 |
| Versene 100 XL | 0.250 | 0.250 | 0.250 | 0.250 | 0.250 | 0.250 | 0.250 |
| Aloe Con UP-40 Cos** | 0.010 | 0.010 | 0.010 | 0.010 | 0.01a | 0.010 | 0.010 |
| Vitamin E Acetate | 0.010 | 0.010 | 0.010 | 0.010 | 0.010 | 0.010 | 0.010 |
| Fragrance | 0.200 | 0.200 | 0.200 | 0.200 | 0.200 | 0.200 | 0.200 |
| Glycerin | 0.500 | 0.500 | 0.500 | 0.500 | a.500 | 0.500 | 0.500 |
| Citric Acid, USP | 0.025 | 0.025 | 0.025 | 0.025 | 0.025 | 0.025 | 0.025 |
| Water | Q.S to 100 | Q.S. to 100 | Q.S. to 100 | Q.S. to 100 | Q.S. to 100 | Q.S. to 100 | Q.S. to 100 |

TABLE 4

Comparative Example 1

| Ingredient Trade Name | Component INCI Name | % WT/WT |
|---|---|---|
| DI Water | Water | 58.2268 |
| Tegobetaine L-7 | Cocamidopropyl Betaine | 12.5000 |
| Cedepal TD403 | Sodium Trideceth Sulfate | 9.0000 |
| Monateric 949-J | Disodium Lauroamphodiacetate | 2.7000 |
| Atlas G-4280 | Poiyoxyethiene (80) Sorbitan Monolaurate | 6.3000 |
| Dowicil 200 | Quaternium-15 | 0.9500 |
| Versene 100 XL | Tetrasodium EDTA | 0.2500 |
| Plantaren 1200* | Lauryl Polyglucose | 5.0000 |
| Euperlan PK3000 | Glycol Distearate (and) Laureth-4 (and) Cocamidopropyl Betaine | 2.5000 |
| Fragrance |  | 0.2000 |
| Abil Quat 3474* | Quaternium 80 | 0.2500 |
| Antil 171 Liquid* | PEG-18 Glyceryl Glycol Dioleococoate | 2.0000 |

TABLE 4-continued

Comparative Example 1

| Ingredient Trade Name | Component INCI Name | % WT/WT |
|---|---|---|
| NaOH | sodium hydroxide | 0.0232 |
| Amilion GST-40 | Laureth-3 (and) Glyceryl stearate/Diacetytartrate | 1.0000 |
| | TOTAL | 100.0000% |

The cleansing composition shown in Example 1 is prepared as follows:

Preparation of Sandopan LS-24 pre-mix

Component amounts in this procedure are given in terms of parts by weight to prepare 100 parts of the pre-mix. 66.57 parts of water are heated to a temperature of 155 to 170° F. 33.33 parts of Sandopan LS-24 are added with agitation. The temperature is maintained at 155 to 170° F. until all of the Sandopan has dissolved. The temperature is then cooled to below 110° F. and 0.10 parts of Dowicil 200 are added; agitation is continued until the premix is uniform.

Main compounding step

Component amounts in this procedure are given in terms of parts by weight to prepare 100 parts of the cleansing composition of Example 1. 27.6 parts water are heated to 145 to 150° F. with agitation. 0.4 parts PEG 6000 distearate are added with agitation until all of the PEG 6000 distearate has dissolved. 1.0 parts Glucquat 125 is added with continued agitation until a uniform mixture is obtained. Cooling is commenced and the following are added simultaneously:

33.7 parts water 12.5 parts Tegobetaine L-7

2.7 parts Monateric 949-J 9.0 parts Cedapal TD 403

5.8 parts Atlas G-4280

During the addition of the above ingredients, the following are also added:

2.0 parts Culinox 999

1.35 parts of the Sandopan LS-24 pre-mix 0.5 parts glycerin

When the temperature has cooled to below 120° F., 0.2 parts of fragrance pre-blended with 0.5 parts Atlas G-4280 are added. The following items are then added:

0.05 parts Dowicil 200

0.14 parts Versene 100XL 0.1 parts Aloe CON UP-40 Cos 0.01 parts Vitamin E acetate When the temperature has cooled to below 89° F., 2.5 parts of Euperlan PK-3000 are added with continued stirring. The pH of the composition is adjusted with a 20% citric acid solution until a final pH of 6.8 to 7.2 is obtained.

The degree of moisturization imparted by a moisturizing cleanser can be assessed by measuring the amount of water on the skin surface following the use of the moisturizing cleanser. The water content of the skin has been shown to be related to the skin's electrical properties. The measurement of impedance of the skin (the total electrical resistance of the skin to an alternating current) has been studied extensively and has been widely used to assess the hydration state of the skin's surface (J. Serup and G. B. E. Jemec in Handbook of Non-Invasive Methods for the Skin, CRC Press Inc., Boca Raton, Fla., 1995, the disclosure of which is hereby incorporated by reference). Skin surface capacitance measurements were made with a Nova Technology Corp. Model 9003 dermal phase meter (DPM) equipped with a DPM 9103 remote sensor probe (Nova Technology Corporation, Gloucester, Mass.). This device emits a 1 Mhz span of simultaneously produced frequencies, producing a differential current source using a controlled rise time. The sensor probe has 2 concentric brass electrodes which are separated by a non-conducting resin. The DPM measures and reports capacitance values at several frequencies from the signal-phase delay data. The capacitance readings are directly related to picoFarads (pF) of capacitance in the volume of skin that is effectively measured. Conductance and capacitance have been shown to correlate to skin water content in vivo and the capacitance values delivered by the instrument are representative of the hydration state of the upper stratum corneum, i.e., the upper layers of the skin (P. Treffel and B. Gabard, "Stratum Corneum dynamic Functional Measurements after Moisturizer or Irritant Application", Arch. Dermatol. Res., 287, 474–479, 1995 the disclosure of which is hereby incorporated by reference).

The following test protocol was used to make skin moisture measurements. Subjects who had applied lotions or oils to their skin since their last cleansing were asked to wash both volar forearms with a cleansing bar soap and to rinse and dry their forearms. Baseline readings were taken in four places within a 4×6 cm area on both forearms of each subject prior to treatment with the compositions of this invention. Both forearms of each subject were moistened with warm (approximately 38° C.) tap water. 0.5 ml of the composition of Example 1 was applied to the treatment area on one forearm of each subject over a one minute period and subsequently left in place for three minutes while the untreated arm, moistened with water, served as a control. Both arms were then simultaneously rinsed in separate buckets of warm water for 30 seconds. The arms were then air dried for five minutes. Four readings were then taken on each forearm at three succeeding five-minute intervals following the rinse step, i.e., at 5, 10 and 15 minutes following rinsing, with the probe being wiped between arm changes. Average values were calculated for each arm at each time interval.

Figure 1:
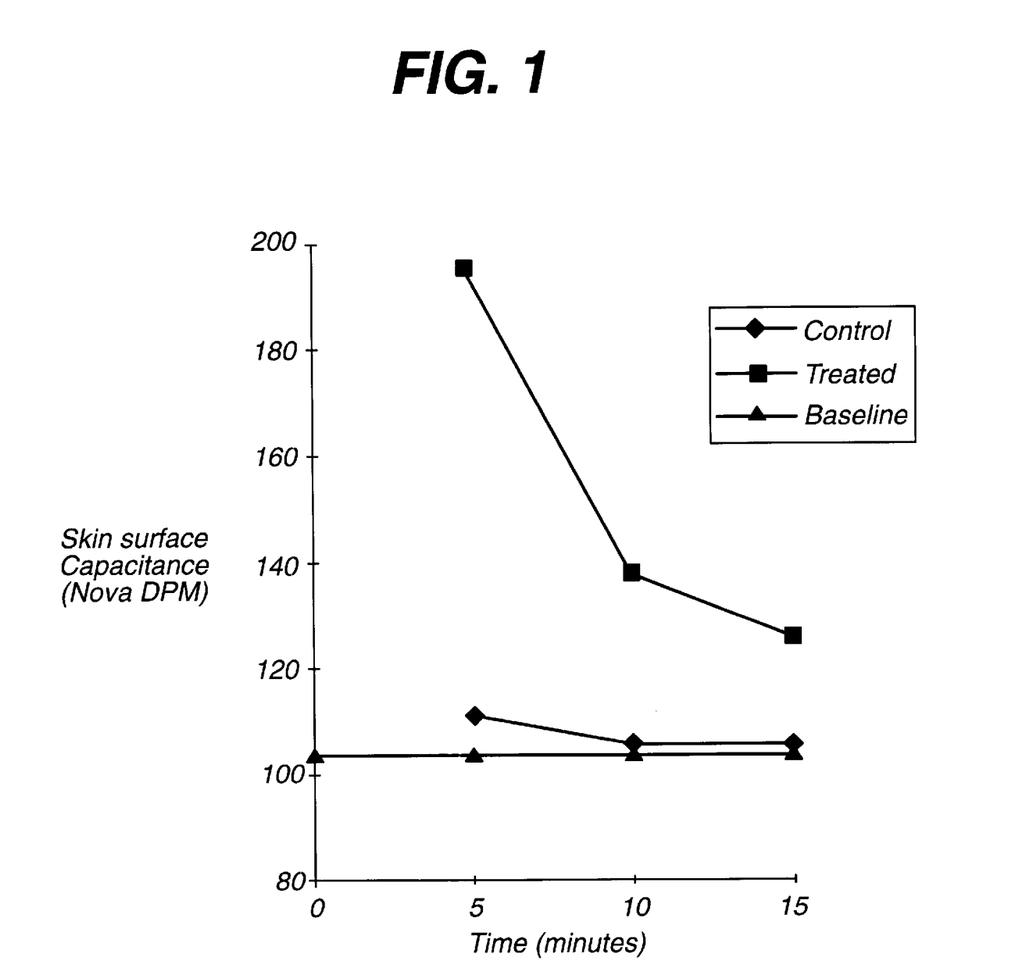
FIG. 1 shows the capacitance of skin as measured after treatment with the cleansing and moisturizing surfactant compositions of the present invention.

The results of these measurements are shown in FIG. 1. Data points represented by triangles, diamonds and squares in FIG. 1 are for baseline measurements, control measurements and measurements after exposure to the composition of Example 1, respectively. It is evident from FIG. 1 that the capacitance, and hence the moisture content of the skin in areas treated with the composition of this invention was significantly higher than the moisture content of the skin in the control area treated with water only. In contrast, the water treated areas showed no significant increase in moisture relative to the baseline values. The increase in moisturization in the treated areas vs. the control was statistically significant at the 99% confidence level after 5 and 10 minutes, and significant at the 95% confidence level after 15 minutes.

The compositions of this invention also exhibit very low irritation to the eyes and skin. Irritation has been measured in accordance with the Invittox Protocol Number 86, the "Trans-epithelial Permeability (TEP) Assay". In accordance with the TEP Assay, the ocular irritation potential of a product can be evaluated by determining its effect on the permeability of a cell layer, as assessed by the leakage of fluorescein through the layer. In accordance with this in vitro method, monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined by spectrophotometry. The fluorescein leakage is plotted against the concentration of test material to determine the $EC_{50}$ (the concentration of test material that causes 50% of maximum dye leakage, i.e., 50% damage to the permeability barrier). The test procedure is set forth in Invittox Protocol Number 86 (May 1994), the disclosure of which is hereby incorporated by reference.

Exposure of a layer of MDCK cells grown on a microporous membrane to test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well. Generally, a passing score is reflected in an $EC_{50}$ of 2.2 or higher. The composition of Example 1 made in accordance with the present invention had a passing TEP score of 2.98±0.48. In contrast, the composition of Comparative Example 1, which contained, among other ingredients, a cationic silicone (i.e., Quaternium 80) but did not include the cationic polyol i.e., Glucquat 125, used in the compositions of the present invention, scored a failing TEP score of 1.73. These data demonstrate the critical effect of the formulation components on TEP and hence eye irritation, and demonstrate that the compositions of the present invention are exceptionally mild to the eyes.

EXAMPLES 2–9

Cleansing compositions having the formulations set forth in Tables 2 and 3 are made in accordance with the procedure of Example 1.

These compositions are effective for cleansing, conditioning, and moisturizing skin and hair without ocular irritation.

What is claimed is:

1. A composition which imparts cleansing, conditioning and moisturization of the skin and hair and which exhibits a low degree of irritation to the eyes comprising:
   A. a nonionic surfactant comprising a polyoxyethylene derivative of polyol ester wherein
      1. the polyoxyethylene derivative of polyol ester is derived from a polyol selected from sorbitol, sorbitan or mixtures thereof,
      2. the polyoxyethylene derivative of polyol ester contains from about 20 to about 80 oxyethylene units,
      3. the polyoxyethylene derivative of polyol ester is derived from lauric acid,
      3. the polyoxyethylene derivative of polyol ester is derived from lauric acid,
      4. the polyoxyethylene derivative of polyol ester has from about 1 to about 2 lauric acid residues per molecule of polyoxyethylene derivative of polyol ester,
   wherein the nonionic surfactant is present in the composition at a concentration of from about 2 to about 10 percent by weight;
   B. an amphoteric amphocarboxylate surfactant comprising a compound of the formula wherein R is an alkyl group having 11 carbon atoms, x is 2, $R_1$ is hydrogen, $R_2$ is a group of the formula wherein $R_4$ is a 2 carbon alkylene group and $R_3$ is a carboxymethyl group,
   wherein the amphoteric amphocarboxylate surfactant is present in the composition at a concentration from about 0.25 to about 5 percent by weight;
   C. one or more betaine surfactants selected from:
      1. an alkylbetaine of the formula wherein R is a lauryl group having about 12 carbon atoms, and $R_1$ and $R_2$ are each methyl groups,
      2. an amidoalkyl betaine of the formula wherein RCO represents the fatty acid derived from coconut oil, n is 3 and $R_1$ and $R_2$ are each methyl groups, and
      3. mixtures thereof,
   wherein the betaine surfactant is present in the composition at a concentration from about 0.5 to about 8 percent by weight;
   D. one or more anionic surfactants comprising alkyl ether sulfate of the formula wherein
      R is an alkyl group having about 12 to about 13 carbon atoms,
      X is sodium ion and p is an integer from about 1 to about 4,
   wherein the anionic surfactant is present in the composition at a concentration from about 1 to about 8 percent by weight;
   E. a substantive humectant of the formula wherein w+x+y+z=about 10;
   F. a thickener comprising a stearate diester of polyethylene glycol of formula wherein n is 150
   wherein the thickener is present in the composition at a concentration of about 0.1 to about 3 percent by weight,
      said nonionic, amphoteric amphocarboxylate, betaine and anionic surfactants comprising a total of about 5 to about 20 percent by weight of the composition and said substantive humectant comprising from about 0.01 to about 3.0 percent by weight of the composition.

2. The composition of claim 1 further comprising an alkyl ether carboxylate of the formula R(OCH$_2$CH$_2$)$_p$O(CH$_2$)$_n$CO$_2$X wherein R is a lauryl group, X is a sodium ion, p is about 12 to about 14 and n is 1, and wherein the alkyl ether carboxylate comprises from about 0.1 to about 2.5 percent by weight of the composition.

3. The composition of claim 1 further comprising sodium chloride at a concentration of about 0.5 to about 5.0 percent by weight.

4. The composition of claim 1 further comprising a pearlescent or opacifying agent comprising ethylene glycol distearate wherein the pearlescent or opacifying agent is present in the composition at a concentration of about 0.25 to about 2 percent by weight.

5. The composition of claim 1 further comprising aloe vera gel at a concentration of about 0.1 to about 10.0 percent by weight and vitamin E acetate at a concentration from about 0.005 to about 0.25 percent by weight.

6. The composition of claim 1 further comprising glycerin at a concentration of about 0.1 to about 1.0 percent by weight.

7. The composition of claim 1 further comprising one or more additives selected from colorants, fragrances, preservatives, pH adjusting agents or mixtures thereof.

8. The composition of claim 1 having a pH in the range of about 5 to about 7.5.

9. The composition of claim 1 having a Brookfield viscosity in the range of about 500 to about 10000 centipoise.

10. The composition of claim 4 wherein the pearlescent or opacifying agent is added to the composition as a preformed, stabilized aqueous dispersion.

11. The composition of claim 1 wherein
A. the nonionic surfactant is present in the composition at a concentration of about 4 to about 5 percent by weight;
B. the amphoteric amphocarboxylate surfactant is present in the composition at a concentration of about 0.5 to about 1.5 percent by weight;
C. the betaine is cocamidopropyl betaine of the formula R—CO—NH(CH$_2$)$_n$—N$^+$R$_1$R$_2$CH$_2$CO$_2$$^-$ wherein RCO represents the fatty acid derived from coconut oil, n is 3 and R$_1$ and R$_2$ are each methyl groups, and the betaine is present in the composition at a concentration of about 3 to about 5 percent by weight;
D. the anionic surfactant is sodium trideceth sulfate having the formula R(OCH$_2$CH$_2$)$_p$OSO$_3$X wherein R is an alkyl group having about 13 carbon atoms, X is sodium ion and p is an integer from about 1 to about 4, and is present in the composition at a concentration of about 2.5 to about 3.5 percent by weight;

E. the substantive humectant is of the formula wherein w+x+y+z=about 10 and is present in the composition at a concentration of about 0.1 to about 0.5 percent by weight;
F. the thickener is present in the composition at a concentration of about 0.25 to about 1 percent by weight;
G. the composition further comprises glycerine at a concentration of about 0.25 to about 1.5 percent by weight;
H. the composition further comprises sodium chloride at a concentration of about 1 to about 3 percent by weight;
I. the composition further comprises an alkyl ether carboxylate of the formula R(OCH$_2$CH$_2$)$_p$O(CH$_2$)$_n$CO$_2$X wherein R is a lauryl group, X is a sodium ion, p is about 12 to about 14 and n is 1, and wherein the alkyl ether carboxylate comprises from about 0.1 to about 1.0 percent by weight of the composition;
J. the composition has a pH of about 5 to about 7.5 and a Brookfield viscosity of about 500 to about 10000 centipoise.

12. The composition of claim 11 further comprising ethyleneglycol distearate at a concentration of about 0.25 to about 1.0 percent by weight, aloe vera gel at a concentration of about 0.25 to about 1.0% by weight and vitamin E acetate at a concentration of about 0.005 to about 0.1 percent by weight.

13. The composition of claim 1 wherein
A. the nonionic surfactant is present in the composition at a concentration of about 4 to about 6 percent by weight,
B. the amphoteric amphocarboxylate surfactant is present in the composition at a concentration of 1.5 to about 3 percent by weight,
C. the betaine is lauryl betaine of the formula

R—N$^+$R$_1$R$_2$CH$_2$CO$_2$ wherein R is a lauryl group and R$_1$ and R$_2$ are each methyl groups, and is present in the composition at a concentration of about 0.5 to about 3 percent by weight,
D. the anionic surfactant is sodium laureth sulfate having the formula R(OCH$_2$CH$_2$)$_p$OSO$_3$X wherein R is a lauryl group, X is sodium ion and p is an integer from about 1 to about 4, and is present in the composition at a concentration of about 2 to about 4 percent by weight, E. the substantive humectant is on the formula wherein w+x+y+x=about 10 and is present in the composition at a concentration of 0.1 to about 0.5 percent by weight;

F. the thickener is present in the composition at a concentration of about 0.25 to about 1 percent by weight;

G. the composition further comprises glycerine at a concentration of about 0.25 to about 1.5 percent by weight;

H. the composition further comprises sodium chloride at a concentration of about 1 to about 3 percent by weight;

I. the composition further comprises an alkyl ether carboxylate of the formula wherein R is a lauryl group, X is a sodium ion, p is about 12 to about 14 and n is 1, and wherein the alkyl ether carboxylate comprises from about 0.1 to about 1.0 percent by weight of the composition;

J. the composition has a pH of about 5 to about 7.5 and a Brookfield viscosity of about 500 to about 10000 centipoise.

14. The composition of claim 13 further comprising ethyleneglycol distearate at a concentration of about 0.25 to about 1.0 percent by weight, aloe vera gel at a concentration of about 0.25 to about 1.0% by weight and vitamin E acetate at a concentration of about 0.005 to about 0.1 percent by weight.

* * * * *

UNITED STATES PATENT AND TRADEMARK OFFICE
CERTIFICATE OF CORRECTION

PATENT NO. : 6,046,145
DATED : April 4, 2000
INVENTOR(S) : Delores M. Santora and Diana L. Friscia It is certified that error appears in the above-identified patent and that said Letters Patent is hereby corrected as shown below:

Column 17, claim 1,
Lines 59 and 60, "3. The polyoxyethylene derivative of polyol ester is derived from lauric acid." should be deleted.

Signed and Sealed this

Eighteenth Day of September, 2001

Attest:

*Nicholas P. Godici*

NICHOLAS P. GODICI
*Attesting Officer*   *Acting Director of the United States Patent and Trademark Office*